United States Patent
Abichandani et al.

[11] Patent Number: 5,998,688
[45] Date of Patent: Dec. 7, 1999

[54] XYLENE ISOMERIZATION PROCESS USING TOLUENE CO-FEED

[75] Inventors: Jeevan S. Abichandani, Voorhees; Jeffrey S. Beck, Burlington; Stephen H. Brown, Princeton; Ronald J. Cimini, Sewell; Ivy D. Johnson, Lawrenceville; Selma Kwok, Voorhees; Dimitris K. Liguras, Mantua; David L. Stern, Mount Laurel, all of N.J.

[73] Assignee: Mobil Oil Corporation, Fairfax, Va.

[21] Appl. No.: 09/139,465

[22] Filed: Aug. 25, 1998

[51] Int. Cl.[6] .................. C07C 1/00; C07C 5/22; C07C 4/12

[52] U.S. Cl. .................. 585/481; 585/478; 585/489; 585/319

[58] Field of Search ................... 585/477, 478, 585/479, 481, 319, 489

[56] References Cited

U.S. PATENT DOCUMENTS

| | | | |
|---|---|---|---|
| 4,016,219 | 4/1977 | Kaeding | 260/672 T |
| 4,139,571 | 2/1979 | Riehm | 260/668 A |
| 4,160,788 | 7/1979 | Young | 585/475 |
| 4,182,923 | 1/1980 | Chu | 585/475 |
| 4,224,141 | 9/1980 | Morrison et al. | 208/134 |
| 4,236,996 | 12/1980 | Taak et al. | 208/134 |
| 4,723,049 | 2/1988 | Menard et al. | 585/475 |
| 4,899,011 | 2/1990 | Chu et al. | 585/481 |
| 4,922,055 | 5/1990 | Chu | 585/470 |
| 4,956,511 | 9/1990 | Butler et al. | 585/475 |
| 5,387,732 | 2/1995 | Shamshoum et al. | 585/475 |
| 5,475,180 | 12/1995 | Shamshoum et al. | 585/475 |
| 5,516,956 | 5/1996 | Abichandani et al. | 585/481 |
| 5,625,104 | 4/1997 | Beck et al. | 585/475 |
| 5,689,027 | 11/1997 | Abichandani et al. | 585/481 |
| 5,705,726 | 1/1998 | Abichandani et al. | 585/481 |

FOREIGN PATENT DOCUMENTS

| | | | |
|---|---|---|---|
| 5016780 | 6/1975 | Japan | 585/480 |
| 851576 | 10/1960 | United Kingdom | 585/480 |

*Primary Examiner*—Walter D. Griffin
*Assistant Examiner*—Thuan D. Dang
*Attorney, Agent, or Firm*—Peter W. Roberts; Malcolm D. Keen

[57] ABSTRACT

A method for minimizing the loss of xylenes in an ethylbenzene conversion/isomerization process by adding toluene to the feedstock. The concentration of toluene in the feedstock is increased by co-feeding toluene or by recycling toluene separated from the ethylbenzene conversion reactor effluent. The increased toluene concentration reduces the loss of xylenes during the ethylbenzene conversion reaction and under preferred operating conditions increases the amount of xylenes in the product.

10 Claims, 3 Drawing Sheets

XYLENE ISOMERIZATION PROCESS USING TOLUENE CO-FEED

BACKGROUND OF THE INVENTION

This invention is directed to a method for reducing the loss of xylenes in a process for the catalytic conversion of ethylbenzene coupled with xylene isomerization. More specifically, the invention is directed to a method for reducing the loss of xylenes in an ethylbenzene conversion/xylene isomerization process by increasing the concentration of toluene to the feedstock.

Xylenes and ethylbenzene are $C_8$ benzene homologues having the molecular formula $C_8H_{10}$. The three xylene isomers are ortho-xylene, meta-xylene and para-xylene, which differ in the positions of two methyl groups on the benzene ring. The term mixed xylenes describes a mixture of ethylbenzene and the three xylene isomers. Mixed xylenes are largely derived from petroleum.

Para- and ortho-xylene are valuable chemical intermediates. In the petrochemical complex, they are produced in large part by recovery of these compounds from both the crude distillation and the $C_8$ heart cut of the reformer. Recovery is accomplished via several selective separation processes, such as $C_8$ heart-cut distillation to yield high-purity ortho-xylene ("ortho-splitter"), and selective crystallization or sorption processes. The remainder from these separation technologies involves mostly meta- and ortho-xylene, ethylbenzene, and benzene, with relatively low concentrations of other aromatics.

Several technologies exist for upgrading the chemical value of this recycle stream. For example, there are commercial processes for converting this stream into one containing an equilibrium mixture of xylenes-that is, roughly 50 weight percent (wt %) meta-xylene, and 25 wt % each of para- and ortho-xylene-via isomerization. These processes also reduce the ethylbenzene concentration in this recycle loop through mechanisms such as cracking, or hydrocracking (hydrogenation of the ethylene thus formed from ethylbenzene cracking by means of a functional metal).

Although these processes have been practiced commercially for many years, great improvements could be realized if it were possible to significantly reduce the capital costs of the isomerization complex. The commercial processes that are presently being used require large capacity processing vessels to produce a relatively small amount of product. Therefore, it is desirable to find a method that increases the amount of product that can be produced by existing equipment and also allow new plants using smaller capacity equipment to produce the equivalent amount of product.

The various xylenes may be derived from mixtures of $C_8$ aromatics separated from such raw materials as petroleum naphthas, particularly reformates, usually by selective solvent extraction. The $C_8$ aromatics in such mixtures and their properties are shown below:

|  | Freezing Point (°C.) | Boiling Point (°C.) | Density (Kg/m³) | Equilibrium* Proportion (wt %) |
|---|---|---|---|---|
| Ethylbenzene | −95.0 | 136.2 | 869.9 | 8.5 |
| Para-xylene | 13.2 | 138.5 | 863.9 | 22.3 |
| Meta-xylene | −47.4 | 138.8 | 866.3 | 48.0 |
| Ortho-xylene | −25.4 | 144.0 | 883.1 | 21.2 |
|  |  |  |  | Total 100.0 |

*Calculated thermodynamic equilibria at 850° F. (454° C.).

Principal sources of $C_8$ aromatics mixtures are catalytically reformed naphthas and pyrolysis distillates. The $C_8$ aromatic fractions from these sources vary quite widely in composition but will usually be in the range of 10 wt % to 32 wt % ethylbenzene (EB) with the balance being about 50 wt % meta-xylene and about 25 wt % each of para- and ortho-xylene.

Individual isomer products may be separated from the naturally occurring mixtures by appropriate physical methods. Ethylbenzene may be separated by fractional distillation, although this is a costly operation. Ortho-xylene may be separated by fractional distillation, and it is so produced commercially. Para-xylene may be separated from the mixed isomers by fractional crystallization, selective adsorption, or membrane separation.

As shown above, the boiling point of ethylbenzene is very close to those of para-xylene and meta-xylene. As a result, complete removal of ethylbenzene from the $C_8^+$ aromatics mixture by conventional methods, e.g., distillation, is usually impractical. An ethylbenzene separation column may be used in the isomerizer-separator loop or the ethylbenzene may be converted catalytically in the isomerizer-separator loop.

In many processes for xylene isomerization, the conversion of ethybenzene is not maximized because of the need to control the competing reactions which convert xylenes to less valuable compounds. Thus, when ethylbenzene is catalytically converted, the primary consideration for selecting the operating conditions is to minimize xylene losses from transalkylation of xylenes. The present invention solves this problem, yielding less xylenes loss and potentially more xylenes production, by converting toluene to additional xylenes during the ethylbenzene conversion stage of xylene isomerization processing.

SUMMARY OF THE INVENTION

It has now been discovered that the problems encountered in the prior art can be overcome by the present invention, which provides a method for minimizing the loss of xylenes in an ethylbenzene conversion/xylene isomerization process. The method requires adding toluene to the feedstock for an ethylbenzene conversion/xylene isomerization process which includes an ethylbenzene conversion stare and a xylene isomerization stage, and wherein the feedstock contains $C_8^+$ aromatics and the xylene isomerization stage has an effluent stream. The ethylbenzene conversion/xylene isomerization process uses a molecular sieve, such as ZSM-5.

The toluene concentration in the feedstock can be increased in several different ways so that the feedstock contains from about 1% to about 25% toluene by weight. The toluene concentration can also be increased by adding toluene to the feedstock, either from a source external to the process, or in a preferred embodiment of the invention, from toluene separated from the process effluent stream of the xylene isomerization stage of the process. When toluene is separated from the effluent stream, it is recycled into the feedstock upstream of the ethylbenzene conversion stage of the process. If the feedstock is treated to remove $C_9^+$ aromatics, the toluene is added after these aromatics are removed. In a preferred embodiment of the present invention, toluene is added to the feedstock to provide a toluene concentration of at least 5 wt % of the feedstock.

In one embodiment of the invention, para-xylene is recovered from the feedstock after the $C_9^+$ aromatics and, optionally, the ortho-xylene, have been removed. This is done when para-xylene is the desired product of the process. Para-xylene is removed upstream of the addition of toluene to the feedstock and before the ethylbenzene conversion stage of the process. Para-xylene recovery is accomplished by selective sorption and/or crystallization.

In another embodiment of the invention, $C_9^+$ aromatics and, optionally, ortho-xylene, are removed from the xylene isomerization stage effluent stream before toluene is separated from the effluent. The toluene is then either recycled into the feedstock or taken off as a by-product of the process. Besides toluene, benzene can be removed from the effluent. The depleted effluent (i.e., the effluent after $C_9^+$ aromatics, toluene, benzene, and optionally ortho-xylene, have been removed) can be recycled into the feedstock upstream of the point where para-xylene is removed. The depleted effluent is primarily made up of $C_8$ aromatics. When the depleted effluent is recycled into the feedstock, it makes up between about 15% to about 40% by weight of the feedstock. In a preferred embodiment of the invention, the ratio of depleted effluent recycled into the feedstock to toluene recycled into the feedstock is between about 1 to 1 and about 1 to 10.

The present invention has the advantage of reducing the size of the equipment used in an ethylbenzene conversion/xylene isomerization process. The removal of $C_9^+$ aromatics from the feedstock and, optionally, ortho-xylene, allows a smaller reactor vessel to be used in the ethylbenzene conversion stage of the process. Moreover, increasing the toluene concentration minimizes the loss of xylenes during the ethylbenzene conversion stage of the process and provides for a more efficient production of the desired xylene product. Ethylbenzene conversion/xylene isomerization processes presently being used convert a significant percentage of the xylenes to lower value hydrocarbons during the ethylbenzene conversion stage of the process and as a result, are less efficient than the present invention.

Accordingly, the method disclosed in the present invention is capable of producing xylenes more efficiently and at a reduced cost than the previously known processes by minimizing the loss of xylenes during the process and reducing the size of the vessels required to produce an equivalent amount of xylene product.

These and other advantages of the present invention will be appreciated from the detailed description and examples which are set forth herein. The detailed description and examples enhance the understanding of the invention, but are not intended to limit the scope of the invention.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawing, wherein.

DETAILED DESCRIPTION OF THE PREFERRED EMBODIMENTS

The present invention is a method for reducing xylene-losses, and in preferred embodiments for also producing additional xylenes, in ethylbenzene conversion reactions by adding toluene to the feedstock. It is believed that higher concentrations of toluene suppress side reactions that may occur during the ethylbenzene conversion reaction, such as xylene disproportionation, since toluene is one of the products of such conversion. Several process schemes are proposed which take advantage of this finding, including feeding low concentrations of toluene to the ethylbenzene conversion reactor to minimize xylene loss, and feeding higher concentrations of toluene to the reactor to either generate additional xylenes and/or mitigate xylene loss.

It has also been found that a xylene isomerization and ethylbenzene conversion process which decouples the ethylbenzene conversion of $C_8^+$ reformate from the xylene isomerization stage, and ultimate para-xylene recovery, has significant economic advantages over a "conventional" xylene isomerization process. This new method can also be used to improve product yields in existing "conventional" xylene isomerization complexes.

The process of the present invention is directed to converting high percentages of the ethylbenzene present in mixed ethylbenzene-xylene containing feedstocks, while simultaneously minimizing xylene loss and converting xylenes to approximately the thermal equilibrium concentration. In this way, the volume of any recycle stream and/or the complexity of the separation processes needed in a xylene recovery process are minimized.

Figure 1:
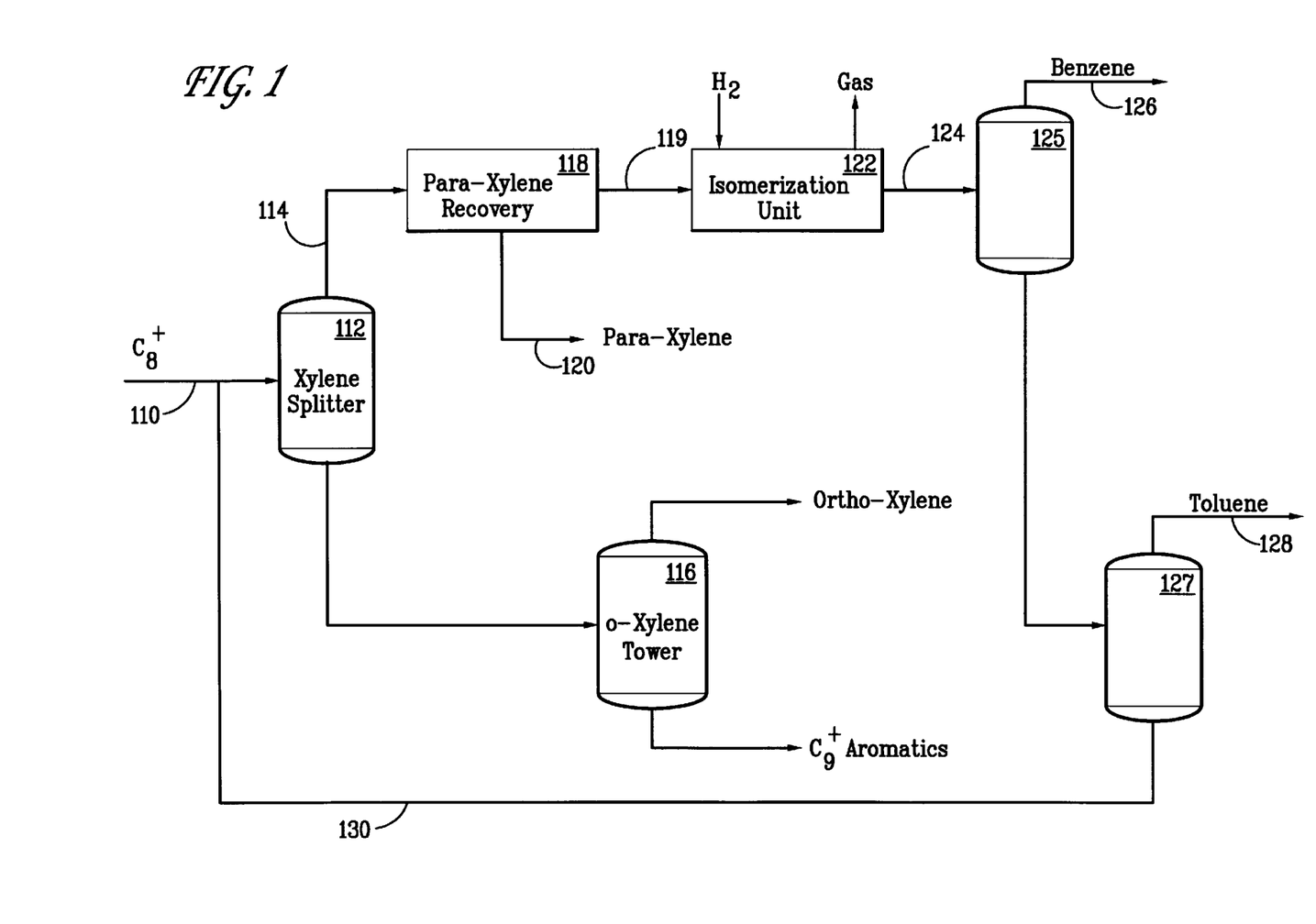
FIG. 1 is a diagram of an ethylbenzene conversion/xylene isomerization process known in the prior art.

FIG. 1 shows a xylene isomerization process known in the prior art wherein a $C_8^+$ aromatics feedstock 110 is fed into a xylene splitter 112, which removes $C_9^+$ aromatics and ortho-xylene from the main feed stream 114. The $C_9^+$ aromatics and ortho-xylene are separated in an ortho-xylene tower 116 and taken off from the process as by-products. The main feed stream 114 is then processed in a para-xylene recovery unit 118 where para-xylene is removed from the feedstock as a product 120. The feedstock is processed in an isomerization unit 122 where xylenes in the feedstock are converted to the thermal equilibrium concentration and substantial amounts of ethylbenzene are converted to benzene and ethane. Benzene 126 and toluene 128 are separated from the effluent of the isomerization unit 124 and the depleted effluent 130 is recycled back into the feedstock 110, upstream of the xylene splitter 112.

Figure 2:
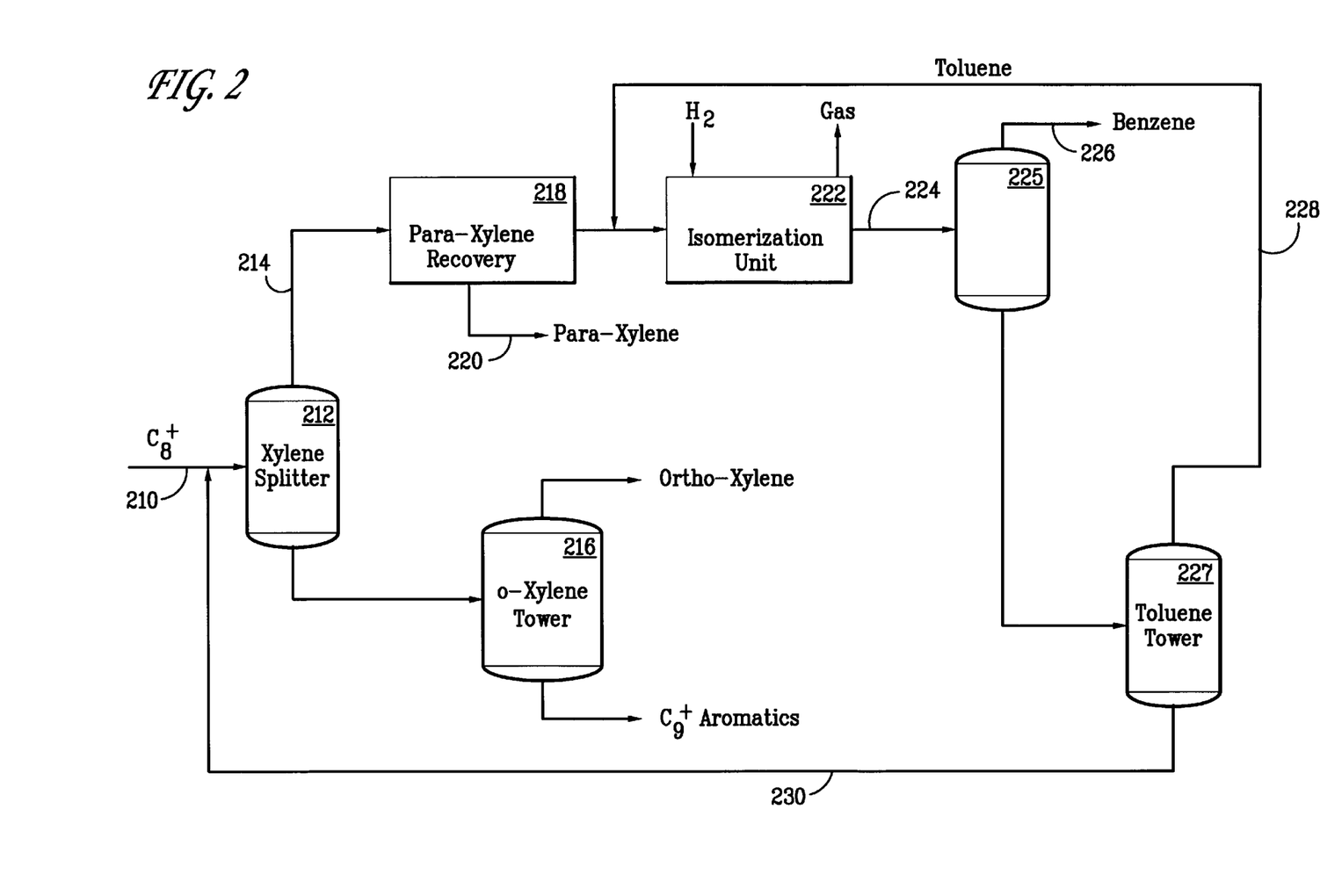
FIG. 2 is a diagram of an ethylbenzene conversion/xylene isomerization process in which toluene recycled into the feedstock.

FIG. 2 shows a preferred embodiment of the xylene isomerization process of the present invention having toluene co-feed. A $C_8^+$ aromatics feedstock 210 is fed into a xylene splitter 212, which removes $C_9^+$ aromatics and ortho-xylene from the main feed stream 214. The $C_9^+$ aromatics and ortho-xylene are separated in an ortho-xylene tower 216 and taken off from the process as by-products. The main feed stream 214 is then processed in a para-xylene recovery unit 218 where para-xylene is removed from the feedstock as a product 220 by selective sorption and/or crystallization. The $C_9^+$ aromatics, ortho-xylene and para-xylene depleted feedstock is processed in an isomerization unit 222 where xylenes in the feedstock are converted to the thermal equilibrium concentration (approximately 50 weight percent (wt %) meta-xylene, and 25 wt % each of para- and ortho-xylene) and ethylbenzene is primarily converted to benzene and ethane. Separators 225 and 227 are used to remove benzene 226 and toluene 228 from the effluent of the isomerization unit 224 and the depleted effluent 230 is recycled back into the feedstock 210, upstream of the xylene splitter 212. The toluene 228 removed from the process is recycled into the feedstock 210 after the para-xylene recovery unit 218 and prior to the isomerization unit 222. It has been found that the increased concentration of toluene in the feedstock 210 minimizes the conversion of xylene to lower order hydrocarbons in the isomerization unit 222 and, thus, increases the xylene production.

Figure 3:
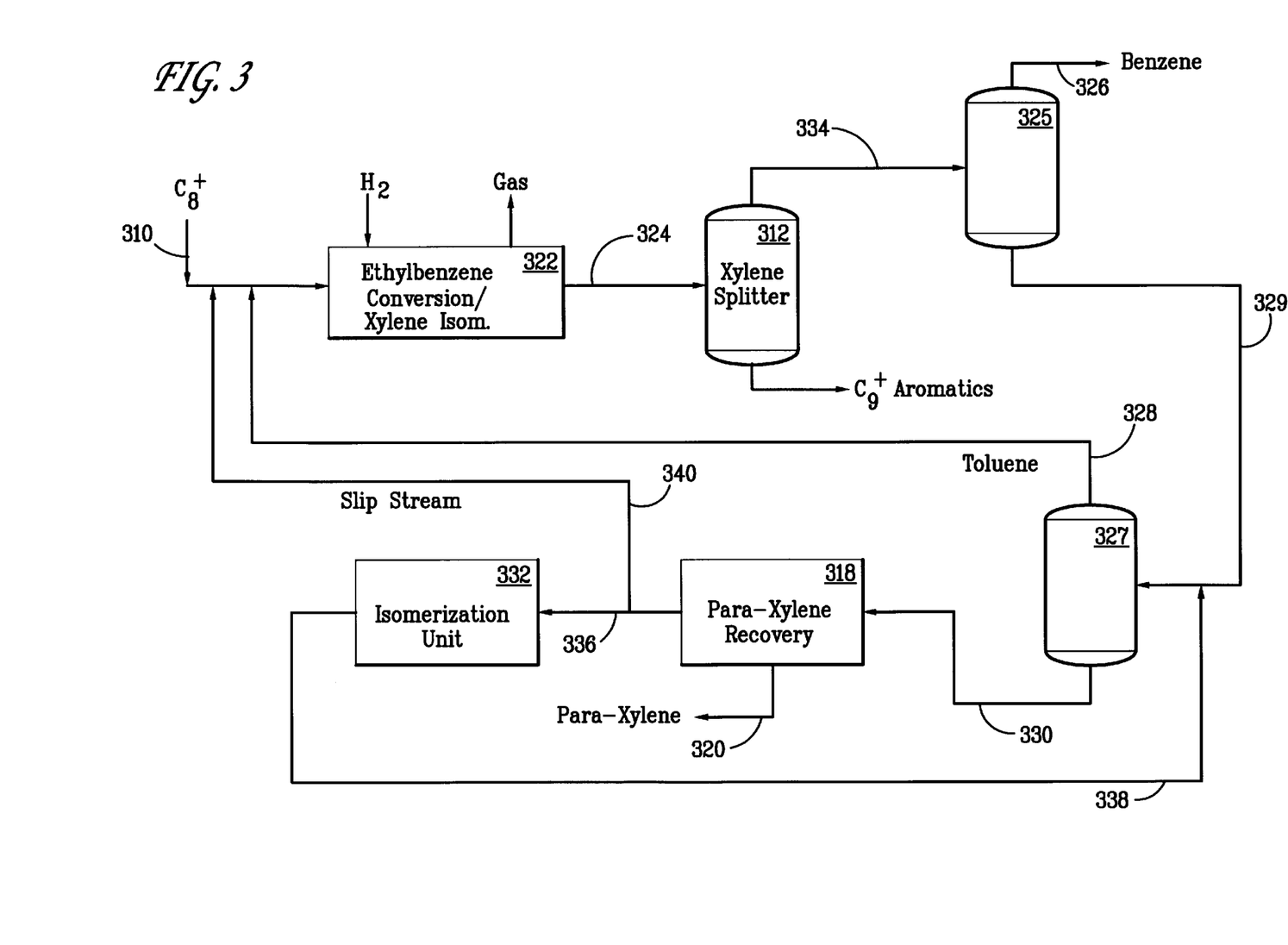
FIG. 3 is a diagram of an ethylbenzene conversion/xylene isomerization process having two stages of xylene isomerization and toluene recycled into the feedstock.

FIG. 3 shows another preferred embodiment of the xylene isomerization process of the present invention which has a second isomerization stage and recycles toluene into the feedstock. A $C_8^+$ aromatics feedstock 310 is fed into an ethylbenzene conversion/xylene isomerization reactor 322 where most of the ethylbenzene in the feedstock is converted to benzene and ethane in a first section of the reactor. The feedstock 310 is then isomerized in the second section of the reactor 322 and xylenes are converted to the thermal equilibrium concentration. The effluent 324 from the ethylbenzene conversion/xylene isomerization reactor 322 is sent to a xylene splitter 312 which removes $C_9^+$ aromatics (and in some embodiments of the invention ortho-xylene) from the feed stream 324 as by-products. Separators 325 and 327 are used to remove benzene 326 and toluene 328 from the $C_9^+$ aromatics depleted effluent 334. The $C_9^+$ aromatics, benzene and toluene depleted effluent 330 is processed in a para-xylene recovery unit 318 where para-xylene is removed as a product 320. The effluent 336 from the para-xylene recovery unit 318, which is primarily comprised of meta-xylene and ortho-xylene, is fed to an isomerization unit 332 where xylenes are converted to the thermal equilibrium concentration and ethylbenzene may be converted to lower order hydrocarbons. The effluent 338 from the isomerization unit 332 is recycled into the $C_9^+$ aromatics depleted effluent 329 of the benzene removal stage 326, prior to the removal of toluene 328. Toluene 328 removed from the effluent 329 is recycled into the feedstock 310 upstream of the ethylbenzene conversion/xylene isomerization reactor 322.

In a particularly preferred embodiment of the present invention, a slip stream 340 of the effluent 336 of the para-xylene recovery unit 318 is recycled into the feedstock 310 upstream of the ethylbenzene conversion/xylene isomerization reactor 322. The slip stream 340 provides the advantage of allowing the feedstock 310 to be enriched with $C_8$ aromatics and also provides a means for controlling the recycling of $C_8$ aromatics through the para-xylene recovery unit 318 and the isomerization unit 332.

The present invention may be incorporated into a new or existing xylene isomerization complex. A conventional xylene isomerization plant, such as that illustrated schematically in FIG. 1, can be modified by adding toluene immediately upstream of the isomerization unit to provide a process as shown in FIG. 2. Such a modification would require minimal capital costs, since the "basic" hardware is already in place. Expected savings for a grass roots design would be even greater.

Catalytic Ethylbenzene Conversion and Xylene Isomerization Reactions $C_8$ aromatics feedstock can be contacted with a catalyst under ethylbenzene conversion conditions to produce an ethylbenzene depleted product. Optionally, toluene can be co-fed with the feedstock to minimize the depletion of para-xylene from the product. The catalyst may be a silica-bound intermediate pore size molecular sieve that has been modified by being exposed to at least two selectivation sequences, each selectivation sequence involves the steps of contacting the molecular sieve with a selectivating agent and subsequently calcining the selectivated molecular sieve.

One mode of ethylbenzene (EB) reduction is through dealkylation to BZ and ethylene (ETH). This reaction can be represented as:

$$EB \rightarrow BZ + ETH \qquad (1)$$

Another reaction for ethylbenzene reduction is through disproportionation to benzene (BZ) and diethylbenzene (DEB). A representation of this reaction is shown by the following equation:

$$EB + EB \rightarrow BZ + DEB \qquad (2)$$

The ethylene produced is saturated to ethane using hydrogen in the presence of a hydrogenation catalyst, such as platinum.

Several side reactions may also take place. Representations for some of the side reactions are given below:

| | | | | | | |
|---|---|---|---|---|---|---|
| TOL | + | TMB | → XYL | + | XYL | (3) |
| TOL | + | TOL | → BZ | + | XYL | (4) |
| EB | + | XYL | → BZ | + | DMEB | (5) |
| EB | + | XYL | → TOL | + | MEB | (6) |
| XYL | + | XYL | → TOL | + | TMB | (7) |
| ETH | + | XYL | → DMEB | | | (8) | wherein: XYL is xylene, DMEB is dimethylethylbenzene, TOL is toluene, MEB is methylethylbenzene, and TMB is trimethylbenzene.

Any reaction leading to a decrease of ethylbenzene in the product or ethylbenzene conversion is referred to herein as "ethylbenzene conversion." Moreover, any reaction leading to a decrease of xylenes or xylene conversion is referred to herein as "xylene conversion." Of these reactions, the reactions in equations 1, 2, 3 and 4 are desirable and the reactions in equations 3 and 4 are the most desirable. However, the reaction in equation 3 is limited by the low percentage of trimethylbenzene in typical feedstocks. Further reactions, such as 5, 6, 7, and 8, are not desirable. In addition to the above described reactions, several types of xylene isomerization reactions may occur contemporaneously. Ethylbenzene conversion and xylene loss, as referred to herein, may be determined by comparing the amount of ethylbenzene and total xylenes in the product stream with the amount of those compounds in the feedstock.

Examples of intermediate pore size zeolites useful in this invention include ZSM-5 (U.S. Pat. Nos. 3,702,886 and Re. 29,948); ZSM-1 (U.S. Pat. No. 3,709,979); ZSM-12 (U.S. Pat. No. 3,832,449); ZSM-22 (U.S. Pat. No. 4,556,477); ZSM-23 (U.S. Pat. No. 4,076,842); ZSM-35 (U.S. Pat. No. 4,016,245); ZSM48 (U.S. Pat. No. 4,397,827); ZSM-57 (U.S. Pat. No. 4,046,685); ZSM-58 (U.S. Pat. No. 4,417,780); and SAPO-5, SAPO-11 and SAPO41 (U.S. Pat. No. 4,440,871). Also, useful in the practice of the present invention are the catalysts disclosed in U.S. Pat. Nos. 4,899,011 and Re. 31,782. The entire contents of the above references are incorporated by reference herein.

A preferred catalyst for the isomerization stage of the process, such as ZSM-5, comprises an intermediate pore size molecular sieve. Preferred catalyst systems for the ethylbenzene conversion stage of the process are disclosed in U.S. Pat. No. 4,899,011, which is incorporated by reference herein. In a most preferred embodiment, the ethylbenzene conversion catalyst is modified by exposure to at least one selectivation sequence. The selectivation sequence includes the steps of contacting the molecular sieve with a selectivating agent and subsequently calcining the selectivated molecular sieve. The intermediate pore size molecular sieve is combined with a silica binder in an amount sufficient to convert at least 50% of the ethylbenzene present in the $C_8$ aromatic mixture to benzene, xylene, or compounds readily removed by distillation from the $C_8$ aromatic mixture. The conversion of at least 50 wt % of the ethylbenzene present in the feedstock may be considered to produce an ethylbenzene-depleted product.

The catalyst is preferably modified in activity and/or selectivity by at least one modification selected from among ex situ selectivation, in situ selectivation, coke selectivation, steaming, adding a hydrogenation/dehydrogenation functional metal, and combinations thereof as well as other techniques that are known in the art. For example, the modified catalyst can comprise a silica-bound intermediate pore size molecular sieve, e.g., ZSM-5, which has been ex situ selectivated by being coated with at least one coating of an organosilicon selectivating agent, wherein each coating of selectivating agent is applied to the molecular sieve by a process including the steps of contacting the catalyst with the organosilicon selectivating agent present in a liquid carrier and subsequently calcining the catalyst in an oxygen-containing atmosphere. The molecular sieve may be combined with the silica binder before or after being coated with the selectivating agent. The molecular sieve may even be combined with the silica binder between subsequent coatings with the selectivating agent. Optionally, the catalyst can be in situ selectivated by being contacted with an organosilicon selectivating agent in a hydrocarbon feedstock under reactor conditions of temperature, pressure, etc., sufficient to deposit a residue of the organosilicon compound on the catalyst. Coke selectivation can be performed by contacting the catalyst with a decomposable organic compound under conditions sufficient to decompose the organic compound while not damaging the catalyst. Steaming can also be performed to modify the activity of the catalyst as is known in the art. Accordingly, by virtue of selective modification of the catalyst, the isomerization process of the present invention exhibits increased selectivity for ethylbenzene conversion and limited xylene isomerization.

The catalyst of the present invention is especially suitable for the conversion of $C_8$ aromatic streams that contain about 1 wt % to about 60 wt % ethylbenzene, e.g., about 1 wt % to about 50 wt % ethylbenzene. This range spans the range of ethylbenzene concentrations of streams that are derived from a reformer and a pyrolysis gasoline unit. The present process may exhibit cracking of normal and branched paraffins of the type present in unextracted $C_8$ aromatic streams.

The performance of a Pt-containing, steamed, silica selectivated catalyst for this reaction is illustrated below in Example 1. Several choices of catalysts may be made for this reaction. For example, the ethylbenzene conversion reactor would preferably use a diffusionally modified catalyst, such as: variations on the multiply ex situ silica-treated catalysts; in situ selectivated catalysts, such as those achieved by co-feeding silicones along with xylenes feed, or a catalyst generated in situ by co-feeding a selectivating agent in an organic or inorganic carrier; a catalyst which has been modified in the reactor by in situ coking; a catalyst which has been modified by inorganic oxides other than silica, etc. The catalyst systems similar to those taught in U.S. Pat. No. 4,899,011 will also work for this invention, and are a preferred embodiment. These catalysts contain a metal for ethylene saturation, such as Pt, Pd, Re, Rd, Fe, W and Ni. Additionally, catalysts that can convert ethylbenzene to xylenes would be useful here. Included in this would be AlPO's, SAPO's, as well as zeolites. A second catalyst may be employed in this ethylbenzene conversion reactor for isomerizing the entering xylenes to equilibrium. Preferred catalysts for this application include the broad class of molecular sieves, including zeolites, SAPO's, AlPO's; solid acids such as tungsten zirconia, etc. A preferable catalyst would be ZSM-5 based.

Feedstock

In general, any aromatic $C_8$ mixture containing ethylbenzene and a xylene may be used as feedstock to the process of this invention. Generally, such a feedstock mixture will typically have a $C_9^+$ aromatics content of from about 0 wt % to about 30 wt %, an ethylbenzene content of about 5 wt % to about 50 wt %, an ortho-xylene content of about 0 wt % to about 35 wt % a meta-xylene content of about 20 to about 90 wt % and para-xylene content of about 0 wt % to about 25 wt %. For example, the feedstock may contain about 10 wt % to about 15 wt % ethylbenzene with the balance made up of xylenes and $C_9^+$ aromatics.

Preferably, the feedstock will contain at least about 30 wt %, more preferably at least about 50 wt %, meta-xylene. Feedstocks meeting this standard are termed "meta-xylene-rich" feedstocks. For example, the feedstock may comprise about 0 wt % to about 30 wt % $C_9^+$aromatics, 1 wt % to about 20 wt % ethylbenzene, about 20 wt % to about 80 wt % meta-xylene, about 5 wt % to about 30 wt % ortho-xylene, and about 0.5 wt % to about 20 wt % para-xylene. Alternatively, the feedstock can comprise about 0 wt % to about 30 wt % $C_9^+$ aromatics, 1 wt % to about 20 wt % ethylbenzene, about 50 wt % to about 65 wt % meta-xylene, about 10 wt % to about 30 wt % ortho-xylene, and about 0.5 wt % to about 5 wt % para-xylene.

In preferred embodiments of the invention, toluene is added to the feedstock to minimize the loss of xylenes, and preferably to increase the xylene content in the effluent. In a most preferred embodiment, the toluene is separated from the effluent of the ethylbenzene conversion reactor and recycled into the feedstock. In addition to the $C_8$ aromatic mixture described above, the feedstock may contain non-aromatic hydrocarbons, i.e., naphthenes and paraffins in an amount up to about 30 wt %. In a preferred embodiment, the invention provides means to process a mixture of $C_8$ aromatics such as that derived after other known processing steps.

Process Conditions

In accordance with the present invention, the above described feedstock may be contacted with the catalyst system under suitable conversion conditions to effect ethylbenzene conversion and to minimize xylene losses. Conditions effective to accomplish ethylbenzene conversion are termed "ethylbenzene conversion conditions." Such conversion conditions can include a temperature of about 200° C. to about 550° C., a pressure of from 0 psig to about 1,000 psig, a WHSV of between about 0.1 hr$^{-1}$ and about 200 hr$^{-1}$, and an $H_2$/HC molar ratio of between about 0.2 and about 10. An alternative to these conversion conditions may include a temperature of about 325° C. to about 475° C., a pressure of about 50 psig to about 400 psig, a WHSV of between about 3 hr$^{-1}$ and about 50 hr$^{-1}$, and an $H_2$/HC molar ratio of between about 1 and about 5. The WHSV is based on the weight of catalyst composition, i.e., the total weight of active catalyst and, if used, binder therefor.

To effect high levels of conversion of ethylbenzene, without excessive loss of xylenes, the feedstock should be contacted with the catalyst under the ethylbenzene conversion conditions described above. The conversion process described herein may be carried out as a batch type, semi-continuous, or continuous operation. After use in a moving or fluidized bed reactor, the catalyst can be regenerated, in a regeneration zone in which the coke is burned from the catalyst in an oxygen-containing atmosphere, e.g., air, at an elevated temperature after which the regenerated catalyst is recycled to the conversion zone for further contact with charge stock. In a fixed bed reactor, regeneration can be carried out in a conventional manner by using initially an inert gas containing a small amount of oxygen (0.5 to 2 volume percent) to burn coke in a controlled manner to limit the temperature to a maximum of about 450° C. to 500° C.

One result of the process of this invention is the conversion of 15% to 100% of the ethylbenzene contained in the mixed xylene feedstock to benzene, ethane and small amounts of other components that are more easily removed from the mixed xylene stream. For example, ethylbenzene conversion levels of greater than 50% are easily accomplished, e.g., greater than 70%, e.g., greater than 80%, e.g., greater than 85%, e.g., 90% or more by weight. The high conversion of ethylbenzene using the selective catalyst and conversion conditions of the present invention results in a molar ratio of benzene produced to ethylbenzene consumed of greater than 0.5, e.g., greater than 0.65, e.g., greater than 0.75, e.g., greater than 0.80.

EXAMPLE 1

A catalyst was modified to promote ethylbenzene conversion and to isomerize xylenes to equilibrium. A silica-bound ZSM-5 catalyst was modified by exposing it to a series of four ex situ selectivation treatments, wherein each treatment comprised contacting the catalyst with 7.8 wt % Dow-550 in decane, followed by drying, and sequential calcination in nitrogen and then air. The four-times treated catalyst was then impregnated with an aqueous solution of platinum ($Pt(NH_3)_4(NO_3)_2$) using an incipient wetness impregnation technique to provide about 0.1 wt % Pt. The catalyst was then dried, calcined in air at 350° C for 4 hours, and steamed at 990° F. (532° C.) for 3 hours.

Two grams of the catalyst were mixed with 6 g of sand and loaded into a ⅜" diameter, stainless-steel tube reactor. The reactor was pressurized with nitrogen to 200 psig, and heated to 350° C. Nitrogen feed was then terminated and 100 cc/min of hydrogen was fed to the reactor for 1 hour. The temperature inside the reactor was then raised to 800° F. and feed introduced.

The purpose of this experiment was to demonstrate the decreased loss of xylenes in an ethylbenzene conversion reaction when toluene is used as a co-feed. Accordingly, tests were conducted using two samples, the first sample was comprised primarily of a base xylene blended and alumina percolated prior to use. The second sample was comprised of the first sample with toluene added to increase the toluene concentration from 0.05% to 18.7%. For the second sample, toluene was introduced via a separate feed pump, and was blended prior to entry into the reactor.

The two samples were tested separately and the feeds and products analyzed on-line using a gas chromatograph. The results of the tests are below.

TABLE 1

ETHYLBENZENE CONVERSION AND
XYLENE ISOMERIZATION EVALUATION

|  | Sample No. 1 No Co-Feed | | Sample No. 2 Toluene Co-Feed | |
| --- | --- | --- | --- | --- |
| Conditons | | | | |
| Temperature (° F.) | 760 | | 820 | |
| WHSV (Overall) | 5 | | 10 | |
| Pressure (psig) | 200 | | 200 | |
| H$_2$/HC (molar) | 1 | | 1 | |
| Co-fed Toluene (%) | None | | ~19 | |
|  | Feed (wt %) | Product (wt %) | Feed (wt %) | Product (wt %) |
| Composition | | | | |
| $C_5^-$ | <0.01 | 2.8 | <0.01 | 2.3 |
| Benzene | <0.01 | 7.1 | <0.01 | 6.6 |
| Toluene | 0.05 | 3.7 | 18.7 | 20.3 |
| Ethylbenzene (EB) | 13.8 | 1.6 | 11.2 | 1.1 |
| Para-xylene | 12.9 | 11.9 | 10.5 | 10.4 |
| Meta-xylene | 47.0 | 46.7 | 38.2 | 38.0 |
| Ortho-xylene | 26.3 | 26.0 | 21.4 | 21.2 |
| $C_9^+$ | <0.01 | 0.11 | <0.01 | 0.2 |
| EB Conversion (%) | | 89 | | 90 |

TABLE 1-continued

ETHYLBENZENE CONVERSION AND
XYLENE ISOMERIZATION EVALUATION

| Xylene Loss (%) | 1.7 | 0.8 |
| --- | --- | --- |
| % Para-xylene Loss | 7.3 | 0.4 |

This example clearly shows that co-feeding toluene in a reactor for ethylbenzene conversion significantly reduces xylene loss. It should be noted that the differences in process conditions would not be expected to yield any significant change in xylene loss. It is believed that most, if not all of the observed significant reduction in xylene loss, is attributable to the use of the toluene co-feed.

It is also believed that this would operate in such a fashion as to generate additional xylenes from toluene disproportionation as well, provided that the conditions were suitable for doing so. Further, we anticipate that co-processing of a $C_9^+$ fraction would not significantly impact product yields.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

What is claimed is:

1. A method for improving an ethylbenzene conversion and xylene isomerization process, said method comprising:
    adding toluene to a feedstock;
    subjecting said feedstock to ethylbenzene conversion by contactins said feedstock with a two component catalyst system to produce an effluent; said two component catalyst system including a first component and a second component wherein:
        said first component comprises a zeolite having a constraint index of about 1 to about 12 and an ortho-xylene sorption time of greater than 50 minutes based on its capacity to sorb 30% of the equilibrium capacity of ortho-xylene at 120° C. and at an ortho-xylene partial pressure of 4.5±0.8 mm of mercury and 0.05 to 10 wt % of a hydrozenation component and is effective, under said isomerization conditions, to deethylate benzene; and
        a second component comprises a zeolite having a constraint index within a range of about 1 to about 12 and characterized by a xylene sorption capacity greater than 1 gram/100 grams of zeolite and an ortho-xylene absorption time for 30 percent of said capacity of less than 10 minutes, wherein the sorption capacity and sorption times are measured at 120° C. and a xylene pressure of 4.5±0.8 mm of mercury; and comprises 0.05 to 10 weight percent of a hydrogenative component wherein the amount of said second component in the catalyst system is at least 50 percent by volume of the catalyst system, and wherein isomerization conditions include a temperature of from about 400° to 1000° F., a pressure of from about 0 to 1000 psig, a WHSV of between 0.5 and 100 and a H$_2$/HC molar ratio of between about 0.5 and 10,
    separating toluene from said effluent to produce a toluene depleted stream; and
    isomerizing said toluene depleted stream;
    wherein said feedstock comprises $C_8^+$ aromatics.

2. A method according to claim 1, wherein said toluene is added to provide a toluene concentration of at least about 5 wt % of said feedstock.

3. A method according to claim 1, wherein said toluene addition comprises co-feeding toluene separated from said effluent to said feedstock.

4. A method according to claim 3, which further comprises removing $C_9^+$ aromatics and, optionally, ortho-xylene from said feedstock prior to said co-feeding of toluene.

5. A method according to claim 4, which further comprises recovering para-xylene from said feedstock after removing said $C_9^+$ aromatics and prior to said co-feeding of toluene.

6. A method according to claim 3, which further comprises removing $C_9^+$ aromatics and, optionally, ortho-xylene from said effluent prior to separating said toluene.

7. A method according to claim 6, which farther comprises removing benzene from said effluent and recycling said effluent into said feedstock.

8. A method according to claim 7, wherein between about 15% to about 40% of said feedstock is comprised of said recycled effluent.

9. A method according to claim 1, wherein said feedstock is contacted with said first component of said catalyst system before said feedstock is contacted with said second component of said catalyst system.

10. A method according to claim 1, wherein at least one component of said two component catalyst system further comprises a dehydrogenation component selected from the group consisting of platinum, palladium, rhenium and iridium.

* * * * *

UNITED STATES PATENT AND TRADEMARK OFFICE
CERTIFICATE OF CORRECTION

PATENT NO.   : 5,998,688

DATED        : December 7, 1999

INVENTOR(S)  : Abichandani et al.

It is certified that error appears in the above-identified patent and that said Letters Patent is hereby corrected as shown below:

Claim 1, line 31 "contactins" should be ---contacting---; and

Claim 1, line 41 "hydrozenation" should be ---hydrogenation---.

Signed and Sealed this

Twenty-fifth Day of July, 2000

Attest:

*Attesting Officer*

Q. TODD DICKINSON

*Director of Patents and Trademarks*